United States Patent [19]
Connolly et al.

[11] Patent Number: 5,818,899
[45] Date of Patent: Oct. 6, 1998

[54] X-RAY FLUORESCENCE ANALYSIS OF PULVERIZED COAL

[75] Inventors: Dennis J. Connolly, Alliance; Richard W. Dye, Uniontown; Nicholas J. Mravich, Alliance; Charles C. Stauffer, Beloit; Bart A. Stuchell, Alliance, all of Ohio

[73] Assignee: McDermott Technology, Inc., New Orleans, La.

[21] Appl. No.: 832,425

[22] Filed: Apr. 2, 1997

[51] Int. Cl.[6] .................................................. G01N 23/223
[52] U.S. Cl. .............................................. 375/45; 378/208
[58] Field of Search .................................... 378/44, 45, 47, 378/208

[56] References Cited

U.S. PATENT DOCUMENTS

| | | | |
|---|---|---|---|
| 4,015,124 | 3/1977 | Page | 250/273 |
| 4,063,089 | 12/1977 | Gamba | 250/272 |
| 4,090,074 | 5/1978 | Watt et al. | 250/273 |
| 4,125,769 | 11/1978 | Marten et al. | 250/272 |
| 4,428,902 | 1/1984 | Murray | 376/156 |
| 4,429,409 | 1/1984 | Berry et al. | 378/45 |
| 4,531,093 | 7/1985 | Rollwitz et al. | 324/300 |
| 4,577,338 | 3/1986 | Takahashi et al. | 378/48 |
| 4,841,153 | 6/1989 | Wormald | 250/390.04 |
| 4,846,081 | 7/1989 | Homer et al. | 110/186 |
| 4,867,755 | 9/1989 | Majid et al. | 44/604 |
| 4,893,315 | 1/1990 | Homer et al. | 374/37 |
| 4,895,081 | 1/1990 | Homer et al. | 110/101 |
| 4,916,719 | 4/1990 | Kawatra et al. | 378/46 |
| 5,014,287 | 5/1991 | Thornton et al. | 378/45 |
| 5,065,416 | 11/1991 | Laurila et al. | 378/53 |
| 5,207,507 | 5/1993 | Kimoto et al. | 374/14 |
| 5,253,280 | 10/1993 | Mizuta | 378/45 |
| 5,272,745 | 12/1993 | Smallbone | 378/47 |
| 5,598,451 | 1/1997 | Ohno et al. | 378/44 |

OTHER PUBLICATIONS

ASTM Designation: E 11–87, "Standard Specification for Wire–Cloth Seives for Testing Purposes". pp. 739–741 & Appendix. No date.
ASTM Designation: D 4239–85, "Standard Test Methods for Sulfur in the Analysis Sample of Coal and Coke Using High Temperature Tube Furnace Combustion Methods". pp. 385–393. No date.
Article in *Fossil Plant News*, Spring 1988, "Host Utilities Sought: On–Line Coal Analysis Applications", at p. 3.
Gamma–Metrics, San Diego, CA, "Bulk Material Analyzer Newsletter", No. 5, May 1987, 13 pages.

*Primary Examiner*—David P. Porta
*Attorney, Agent, or Firm*—R. J. Edwards; Eric Marich

[57] ABSTRACT

An on-line X-ray fluorescent monitoring system uses a probe having an X-ray transmitter and a fluorescent X-ray detector placed adjacent a recessed chamber in a coal feed line having an X-ray transparent window. Pulverized coal traveling through the coal feed line collects in the recessed chamber and rests against the X-ray transparent window where it is bombarded by excitation X-rays from the transmitter. The probe receives fluorescence from the X-ray excited coal and transmits the data to a data acquisition and control means for analysis and use. A pressurized air tube is provided at the base of the recessed chamber for blowing accumulated pulverized coal out of the recessed chamber and back into the feed line, thereby allowing a new sample portion of pulverized coal to settle into the recessed chamber for analysis. The on-line analyzer can also be used to determine concentrations of other elements of interest in the pulverized coal, such as iron, chlorine, etc.

12 Claims, 1 Drawing Sheet

X-RAY FLUORESCENCE ANALYSIS OF PULVERIZED COAL

FIELD AND BACKGROUND OF THE INVENTION

The present invention relates generally to the field of chemical analysis of fossil fuels and, in particular, to an on-line X-ray fluorescence monitoring system for determining the sulfur content in a pulverized coal fuel supply.

The amount of sulfur present in coal is an important characteristic of the fuel, especially when the coal is used in industrial or electrical generation power plants. There are two main reasons why sulfur content is important. First, the sulfur content itself is used as an acceptance criteria by the industrial or power plant station when the coal is delivered to the site. Second, the sulfur content is important to the plant operators so that the coal can be burned properly while minimizing emissions of various sulfur compounds ($SO_x$—$SO_2$, $SO_3$, etc.) into the atmosphere as a result of burning the coal.

Most known methods used to analyze the sulfur content of coal samples are complex, elaborate and time-consuming. Commonly, raw coal is brought onto the site for use and dumped into a hopper. The coal is transported from the hoppers to coal pulverizers and it is during this transportation stage that raw coal samples are taken for analysis. To analyze the raw coal samples, the coal must first be crushed and then resampled. This second sampling is collected into approximately 10 gallon containers, which are then further riffled down into a 2 quart size sample. The riffled sample is then submitted to a laboratory for analysis.

The laboratory analysis is conducted using a bench top method in which the coal is ground to a 60 mesh size (250 micron diameter or smaller), dried, and then analyzed using a LECO SC-32 system. The LECO system combusts the dried coal sample in an oxygen atmosphere where the sulfur oxidizes to form $SO_2$. Following the removal of residual moisture and dust, the $SO_2$ gas is measured with a solid state infrared detector. The system is typically microprocessor-based and the analysis results are formulated by combining the outputs of the infrared detector and system ambient sensors with pre-programmed calibration, linearization, and weight compensation factors. These values are then used to calculate and determine the sulfur content of the coal. A primary disadvantage of the LECO system is that it requires the coal be dried prior to testing, and it lacks the ability to perform any type of current or "real-time" analysis of the coal that was sampled.

Representative calorimetry systems employing gravimetric feeders and the like are disclosed in U.S. Pat. Nos. 4,846,081, 4,893,315, and 4,895,081 to Homer et al. Kimoto et al. (U.S. Pat. No. 5,207,507) discloses a thermogravimetric analysis of coal for volatile matter and ash content.

Majid et al. (U.S. Pat. No. 4,867,755) discloses at Col. 5, lines 45–51, that it is well known to employ the ASTM calorimetry method D4329, the LECO sulfur analyzer, or X-ray fluorescence spectroscopy to determine the sulfur content of coke and coke agglomerates. X-ray fluorescence spectroscopy was chosen for this patent because it was stated to provide values closest to the expected sulfur content.

U.S. Pat. No. 4,916,719 to Kawatra et al. discloses an apparatus for the on-line analysis of ash-containing slurries which irradiates slurry samples flowing past a window of a measuring chamber. First and second signals representative of back scattered and iron fluorescent X-rays are used, together with a density measurement made on the sample flowing through the measuring chamber, to determine ash content.

U.S. Pat. No. 4,125,769 to Marten et al. and U.S. Pat. No. 5,065,416 to Laurila et al. each disclose other systems for on-line X-ray fluorescent analysis of slurries.

U.S. Pat. No. 5,272,745 to Smallbone discloses an on-line or in process elemental analysis by X-ray fluorescence spectroscopy particularly adapted to continuously analyze flowing dry powder samples produced by various processes. As disclosed therein at Col. 3, line 49 et seq., the device continuously samples a main product stream and automatically analyzes same. The sample is provided to a cell that is visible to an X-ray analyzer. A feed sample unit is preferably installed above an analyzer sample unit to take advantage of the free flow of powders by gravity, but a small conveyor or other means can be employed to move the feed sample output into the input section of the analyzer sampling unit.

U.S. Pat. No. 4,015,124 to Page is of particular interest because it discloses a method for determining the concentration of sulfur in coal and includes apparatus which enables this method to be put into practice. The method involves measuring the intensities of the X-ray fluorescent radiations from iron and sulfur atoms in a sample of coal which has been excited by X-ray radiation. The measures of the intensities are combined mathematically to give an output from which the concentration of sulfur in the coal may be determined. Using the apparatus described, the concentration of sulfur in the sample of coal can be determined quickly and accurately by an unskilled worker. At Col. 3, line 12 et seq., batch sampling may be used to determine the sulfur content of a large quantity of coal, but continuous sampling is preferable to minimize heterogeneity defects. It is preferred that the sample be ground to a diameter of smaller than 0.5 millimeter, and that for coals with low ash content, the maximum diameter can be 1 millimeter. For coals of the type described it is possible to use particles of a diameter of up to 25 millimeters and that it is preferred that they should not exceed 5 millimeters.

Takahashi et al. (U.S. Pat. No. 4,577,338) discloses an X-ray fluorescence spectrometer and method of calibrating the same which is used to determine the sulfur content of oils and other matrices. Windows through which energy is sampled are adjusted to provide a calibration curve of predetermined shape, and a built in standard is analyzed and the value corresponding to the ratio of relative intensities of the fluorescent energy from the standard and the scattered target line X-ray radiation is stored during initial calibration of the system.

Gamba (U.S. Pat. No. 4,063,089) discloses an X-ray chemical analyzer for field applications that is portable, lightweight and which employs a cryogenically-cooled solid state semiconductor crystal detector for fast in situ analysis of elements in solid, powder, liquid or slurry form. Thornton et al. (U.S. Pat. No. 5,014,287) discloses a portable X-ray fluorescence spectrometer for environmental monitoring of inorganic pollutants.

U.S. Pat. No. 4,428,902 to Murray discloses a system and method for rapidly obtaining quantitative information as to the elemental constituents of coal, particularly the oxygen and sulfur content thereof. It is stated to be particularly useful to the efficient and clean operation of coal-fired power plants. High energy X-rays are used to induce radioactivity in the impurities found in the coal, and the result of the radioactivity is analyzed by suitable gamma ray spectrometer to indicate the amount of impurities present. The coal being analyzed is carried by a conveyor passing through the system.

Watt et al. (U.S. Pat. No. 4,090,074) discloses a method of analyzing coal or coke wherein the concentration of ash or mineral matter is determined from the result of a measurement of the transmission or scatter of X-rays or gamma rays. The coal is being provided on a moving conveyor belt during analysis.

U.S. Pat. No. 4,841,153 to Wormald discloses a method and system for analyzing coal or other materials by neutron bombardment to generate gamma rays which are detected.

U.S. Pat. No. 4,531,093 to Rollwitz et al. is interesting in that it discloses a flow meter apparatus and method for measuring the flow, composition, and heat content of coal through a combination of electron magnetic resonance (EMR) and nuclear magnetic resonance (NMR) analysis of the flowing coal. By calibration utilizing a standard specimen for a given type of coal, a profile for various types of coal can be obtained wherein measurement data is converted into an indication of the heat content in BTU per pound.

U.S. Pat. No. 4,429,409 to Berry et al. discloses a portable apparatus for analyzing a sample material by the X-ray fluorescent method having a hand-held probe unit connected to an electronic unit. The apparatus is particularly directed to the analysis of metals, including alloys identification and analysis. The primary objectives are to verify alloy grade or type used and composition analyses of a large number of engineering alloys.

Mizuta (U.S. Pat. No. 5,253,280) discloses a particular design for a sample cell support assembly for fluorescent X-ray analysis. The sample cell has an inner and an outer cell frame that captures an X-ray transmissive member. A particular object of the invention is to provide a sample cell that will always maintain the sample at a constant distance away from an X-ray detector, regardless of the number of times the sample cell is aligned on the analyzer, to assure accuracy in analysis.

X-ray fluorescence spectroscopy is an attractive analytical method for on-line process applications because it is rapid, non-destructive, and provides simultaneous information on a variety of elemental constituents of a sample. However, the direct analysis of sulfur in pulverized coal in a feed stream by X-ray fluorescence is hampered by two characteristics of the sample. First, sulfur and some other elements of interest in coal are present in low concentrations, often approaching or below the detection limits of X-ray fluorescence. Second, the effective concentration is further decreased by a dilution factor as the coal is distributed in an air stream. The present invention overcomes such analytical difficulties.

SUMMARY OF THE INVENTION

It is an object of the present invention to quickly and simply analyze coal for the concentration of an element of interest, particularly sulfur content.

It is a further object of the invention to analyze the coal as it travels from a pulverizer or supply to a point of combustion in a furnace or boiler for allowing increased control of the combustion parameters, thereby reducing the production of environmentally hazardous sulfur compounds.

Accordingly, one aspect of the present invention is drawn to an on-line analyzer in which an X-ray transmitter and fluorescent X-ray detector probe are placed adjacent a recess in a coal feed line having an X-ray transparent window. Coal traveling through the feed line collects in the recess and rests against the X-ray transparent window where it is bombarded by excitation X-rays from the transmitter. The probe receives fluorescence from the X-ray excited coal and transmits the data to a data acquisition and control device for analysis and use. A pressurized air tube is provided at the base of the recess for blowing accumulated coal out of the recess and back into the feed line, thereby allowing additional coal to settle into the recess for analysis.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

DESCRIPTION OF THE PREFERRED EMBODIMENTS

Figure 1:
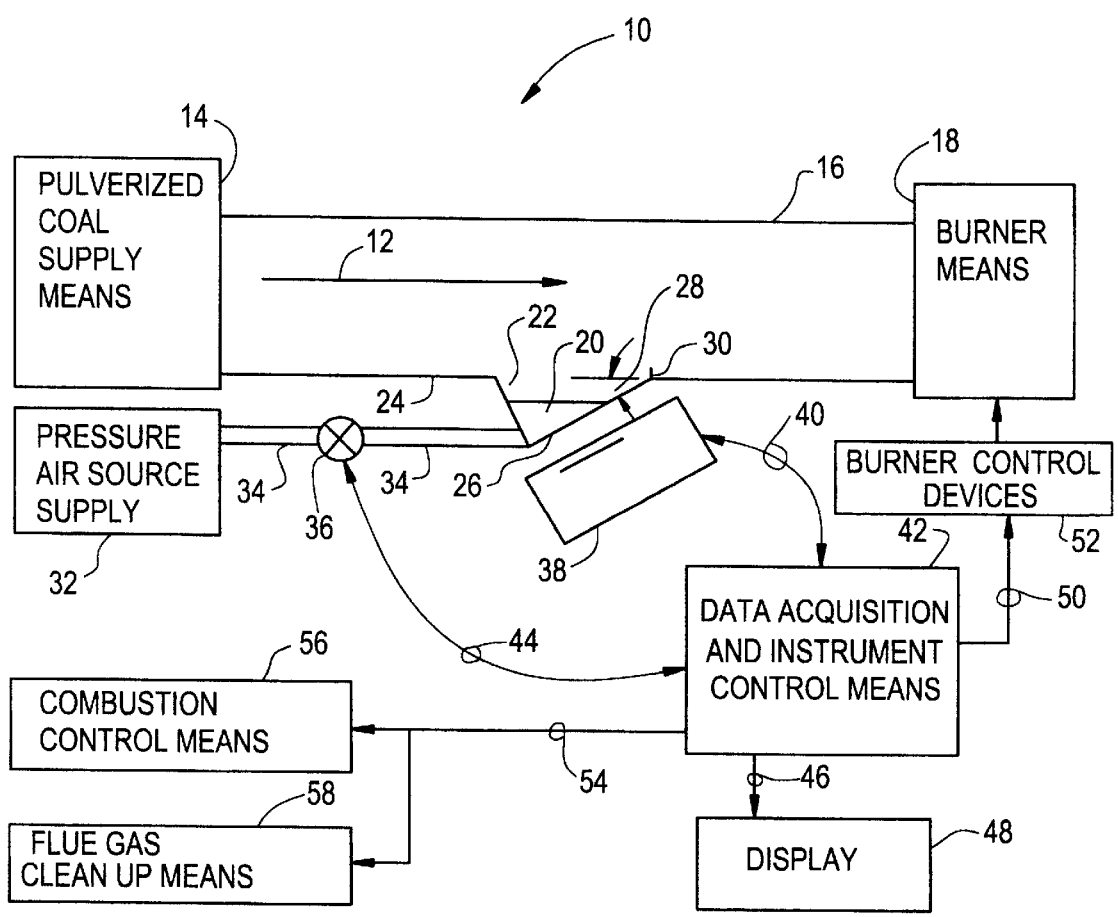
FIG. 1 is a schematic diagram of an on-line X-ray fluorescence monitoring system for determining a concentration of an element of interest in pulverized coal, particularly sulfur content, according to the invention.

Referring now to the drawing, there is shown a schematic diagram of an on-line X-ray fluorescence monitoring system, generally designated 10, for determining a concentration of an element of interest in a flowing stream of pulverized coal 12, according to the invention. While the present invention was primarily developed to analyze this flowing stream of pulverized coal 12 to determine the concentration of sulfur in the pulverized coal 12, and the following discussion is primarily based upon using the system 10 of the invention to determine sulfur concentration, it will be appreciated by those skilled in the art that the invention is not so limited. Any element of interest which is present in the pulverized coal 12 and which can be detected through X-ray fluorescent analysis may be monitored. This would generally include elements having an atomic weight equal to or greater than 11 (sodium, Na), and thus the present invention could be used to advantage to determine concentrations of many of the major constituents which occur in coal ash subsequent to combustion, such as but not limited to silicon (Si), aluminum (Al), iron (Fe), titanium (Ti), calcium (Ca), magnesium (Mg), sodium (Na), potassium (K), sulfur (S), and phosphorous (P). While these elements normally occur in coal ash as oxides, the present invention can be of assistance in determining their presence and concentration in the raw coal and thus could be of use in estimating or possibly predicting the coal ash composition.

The pulverized coal 12 is provided from pulverized coal supply means 14, such as a coal pulverizer, and is conveyed along a conduit or coal feed line 16, such as a burner line, to burner means schematically indicated at 18. The burner means 18 introduces the pulverized coal 12 into a boiler furnace or combustion chamber (not shown) where the pulverized coal 12 is burned to produce heat.

To analyze the pulverized coal 12 for the presence of an element of interest, such as sulfur, a sample 20 of the pulverized coal 12 must be obtained and to that end there is provided a recessed chamber 22 positioned on a wall 24 of the coal feed line 16, at a point between the pulverized coal supply means 14 and the burner means 18, and in the lower portion of the coal feed line 16. Locating the recessed chamber 22 in the lower portion of the coal feed line 16 ensures that the force of gravity will assist in collection of the sample. The recessed chamber 22 forms an essential component of the on-line X-ray fluorescence monitoring system 10 according to the present invention.

The recessed chamber 22 is preferably constructed as an angled portion having an upstream end (with respect to the direction of flow of the pulverized coal 12 through the coal feed line 16) extending outwardly and obliquely from the wall 24 of the coal feed line 16, but other configurations are also possible. The side of the feed line chamber 22 opposite the coal feed line 16 is provided with an X-ray transparent window 26. The X-ray transparent window 26 extends from the wall 24 of the coal feed line 16 at an angle designated 28 as shown in the FIGURE. As the pulverized coal 12 flows through the coal feed line 16, a portion will tend to settle out and collect in a pile in the recessed chamber 22, rather than passing over the recessed chamber 22, and accumulate to form the sample 20 of pulverized coal 12. The sample 20 rests against the X-ray transparent window 26 in a substantially air-free pile.

Angle 28, measured between the side of recessed chamber 22 having the X-ray transparent window 26 relative to the wall 24 of the coal feed line 16 may be adjusted to increase or decrease the size of the recess in recessed chamber 22 and, with it, the amount of the sample 20 of pulverized coal 12 collected therein. If necessary, a small lip 30 may be placed adjacent the downstream side of recessed chamber 22 and extending into the coal feed line 16 to enhance the collection of the flowing pulverized coal 12 within the recessed chamber 22. The recessed collection chamber 22 should be large enough such that the collected amount of pulverized coal 12 in the sample 20 which rests against the X-ray transparent window 26 is considered to be "infinitely thick" as defined in commonly accepted X-ray literature. In this way, the excitation energy impinging on the sample 20 is totally absorbed and there will be no variation of fluorescent signal strength as a function of the thickness of the sample 20; instead, the measured fluorescent signal strength will only be a function of elemental concentration.

Since the present invention is drawn to an on-line monitoring system, periodic measurements of the concentration of the element of interest are necessary and each new measurement will require obtaining a new sample 20 of the pulverized coal 12. To this end there is thus provided means for periodically purging the recessed chamber 22, advantageously comprising a pressurized air source 32 is connected by a purge air tube 34 to a lower end of the recessed chamber 22. A manually or automatically controlled valve 36 is provided in purge air tube 34 to control the flow of air through the purge air tube 34 as necessary. More particularly, when a new sample 20 is desired, the control valve 36 is opened, allowing pressurized air to flow into the lower end of the recessed chamber 22 and into the pile of pulverized coal 12 which has accumulated therein. The pressurized air forces the previously collected sample 20 of pulverized coal 12 out of the recessed chamber 22 and back into the main flow of pulverized coal 12 where it is reentrained and provided on to the burner means 18 for combustion. Once the recessed chamber 22 is flushed or purged by the pressurized air, the control valve 36 is closed to allow the collection of another sample 20 of pulverized coal 12 to begin. At the lower end of the recessed chamber 22, the purge air tube 34 may be connected to one or a plurality of entry openings (not shown) to enhance the evacuation of the recessed chamber 22. As described in greater detail below, the control valve 36 may be manually controlled by a human operator, or it may be controlled via a control signal provided by other elements of the invention so that after an analysis of the sample 20 of collected pulverized coal 12 has occurred, the process may be repeated continuously with or without human operator intervention as desired.

To accomplish the actual measurement of the concentration of the element of interest in the sample 20 of pulverized coal 12, an X-ray probe 38 of known design and construction is placed adjacent the X-ray transparent window 26 of the recessed chamber 22. X-ray probe 38 contains an X-ray excitation source and an X-ray fluorescence detector. A suitable excitation source may be an electronic X-ray tube having either pre-set or variable power or one of any known radioisotopes. In the case of an electronic X-ray tube, the power of the source should be set to maximize the analysis of the element or elements of interest. The radioisotope selected for use should also optimize the analysis.

The fluorescence detector portion of the probe 38 senses a fluorescent signal emitted from the X-ray excited coal through window 26. The window 26 is designed to be highly transparent to X-ray radiation and fluorescence, while having a thickness acceptable for maintaining the integrity of the coal feed line 16. Suitable materials for this purpose include polyimide materials such as KAPTON® (a registered trademark of E. I. duPont de Nemours & Co.), or beryllium, in appropriate thicknesses for the stresses placed on the materials.

The fluorescence detector portion of probe 38 transmits the sensed information via line 40 to data acquisition and instrument control means, generally designated 42. Advantageously, the data acquisition and control means 42 comprises a microprocessor-based computer with provisions for data input, storage, and output, as well as means for human operator interaction such as a keyboard, etc., as well as calculating means for processing the sensed information through programmed algorithms or for comparing the sensed information data against stored values. The data acquisition and instrument control means 42 analyzes the information collected by the detector portion in the probe 38 against pre-calibrated standards and determines the concentration of the element of interest, such as sulfur, in the sample 20 of pulverized coal 12 which had accumulated in the recessed chamber 22. The data acquisition and instrument control means 42 can also be used to control the operation of control valve 36 via line 44, either automatically at predetermined intervals, or at the instruction of a human operator.

The X-ray fluorescent monitoring system 10 of the present invention may be calibrated using powdered coal standards having known sulfur or other elemental concentrations. Such standards may be obtained from NIST or other acceptable suppliers. Standards covering an appropriate range of concentrations may be placed directly into the recessed sample chamber 22 or, alternatively, the recessed sample chamber 22 may be designed as a removable element and the standards may be measured using the removable chamber 22, or a separate recessed sample chamber or container which is of identical size, shape and materials of construction as the recessed chamber 22 of the X-ray fluorescent monitoring system 10. Recording of elemental fluorescent intensities of such standards so measured will allow determination of calibration parameters, in terms of the mathematical definition of the relationship between elemental concentration and resulting fluorescent intensities. These calibration parameters will comprise the slope and intercept of that relationship as well as any curvature (hyperbolic) factor. These calibration parameters may then be input to the data acquisition and instrument control means 42, for automated conversion of the measured raw fluorescent intensities into the corresponding elemental concentrations.

The information representative of the measured elemental concentrations may be provided as an electrical signal representative thereof via a line 46 to analog or digital display means, schematically indicated at 48, for viewing by a human operator, or provided as a control signal along a line 50 to burner control devices schematically shown at 52 to automatically control certain settings of the burner means 18, such as the positions of any associated air registers and the like (not shown). Similar control signals could be provided to other power plant devices to control the rate of fuel and/or air provided to the combustion furnace (not shown), or to control the operation of downstream flue gas pollution control equipment such as scrubbers for flue gas desulfurization (also not shown). This aspect is schematically represented in the FIGURE by line 54 which could provide such control signals there along to such other devices, schematically represented as combustion control means 56 and flue gas cleanup means 58. Naturally, these other devices already have their own control systems and persons skilled in the art would utilize and condition the signals indicative of the measured elemental concentration as required. Even if such signals are not actually integrated into the automatic control of such other devices, provision of a local display of the concentration of the element of interest, such as sulfur, near the operator consoles of these other devices, might be instructive in planning or predicting changes in conditions that might affect these devices.

Accurate readings of the sulfur or other elemental content of the pulverized coal 12 are made possible since air can be eliminated as an interferant by placing the X-ray probe 38 flush against the transparent window 26. It will be appreciated by those skilled in the art that, in practice, the X-ray probe 38 would actually be located very near the X-ray transparent window 26; the space between the window 26 and X-ray probe 38 shown in FIG. 1 is thus somewhat exaggerated for purposes of illustration. Further, air is nearly eliminated from the sample 20 of pulverized coal 12 against the window 26 by the configuration of the recessed chamber 22 in the coal feed line 16. In the case of elements like sulfur, which is light and produces only energetically weak fluorescent signals, the content analysis is greatly enhanced by the elimination of air from the pulverized coal 12 sample 20. By collecting the pulverized coal 12 against the window 26, the sample 20 is also concentrated, increasing the detection of weak signals and allowing rapid and accurate measurements to be taken repeatedly.

As described earlier, persons skilled in the art will also appreciate that the present invention can be used to analyze a flowing stream of pulverized coal for the presence of other elements, such as iron, chlorine, etc. Knowledge of the concentrations of such other elements in the flowing pulverized coal stream, in and of themselves, can have benefits as well. While a specific embodiment of the invention has been shown and described in detail to illustrate the application of the principles of the invention, it will be understood that the invention may be embodied otherwise without departing from such principles.

We claim:

1. An on-line X-ray fluorescence monitoring system for determining a concentration of an element of interest in a pulverized coal, the monitoring system comprising:

a pulverized coal feed line conveying pulverized coal containing an element of interest;

a recessed chamber in the coal feed line for collecting a sample portion of the pulverized coal from the coal feed line of sufficient thickness such that when excitation X-rays are transmitted into the sample portion of pulverized coal in the recessed chamber, there is no variation of X-ray fluorescent signals generated by the sample portion of the pulverized coal in the recessed chamber excited by the excitation X-rays as a function of sample thickness;

an X-ray transparent window forming one side of the recessed chamber;

probe means adjacent the X-ray transparent window for transmitting excitation X-rays through the X-ray transparent window to the sample portion of pulverized coal in the recessed chamber and for receiving X-ray fluorescent signals generated by the sample portion of the pulverized coal in the recessed chamber excited by the excitation X-rays;

data acquisition and instrument control means for determining the concentration of the element of interest in the pulverized coal from the X-ray fluorescent signals received and producing a signal indicative thereof; and flushing means for removing the collected pulverized coal sample portion from the recessed chamber so that a new sample portion of pulverized coal can be collected in the recessed chamber for analysis.

2. The monitoring system according to claim 1, wherein the X-ray transparent window is oriented obliquely to a direction of flow of pulverized coal through the coal feed line.

3. The monitoring system according to claim 2, wherein the flushing means comprises a source of pressurized air connected to the recessed chamber through a valve such that pressurized air is delivered to the recessed chamber when the valve is opened.

4. The monitoring system according to claim 3, wherein the probe means comprises an X-ray excitation source and an X-ray fluorescence receiver.

5. The monitoring system according to claim 4, wherein the X-ray excitation source comprises an electronic X-ray tube.

6. The monitoring system according to claim 4, wherein the X-ray excitation source comprises a radioisotope.

7. The monitoring system according to claim 1, further comprising a lip protruding into the coal feed line adjacent a downstream edge of the recessed chamber.

8. The monitoring system according to claim 1, wherein the data acquisition and instrument control means further comprises control means for controlling the flushing means such that once the data acquisition and instrument control means has determined the concentration of the element of interest in the pulverized coal sample portion in the recessed chamber, the flushing means is activated, allowing a new sample portion of pulverized coal to settle and collect in the recessed chamber for analysis.

9. The monitoring system according to claim 1, further comprising means for providing the signal indicative of the determined concentration of the element of interest to display means for providing a readout of the determined concentration of the element of interest for viewing by a human operator.

10. The monitoring system according to claim 1, further comprising means for providing the signal indicative of the determined concentration of the element of interest as a control signal to burner control devices and to other equipment associated with the combustion process.

11. The monitoring system according to claim 1, wherein the element of interest is a member selected from the group consisting of sulfur, iron, and chlorine.

12. The monitoring system according to claim 1, wherein the element of interest which is present in the pulverized coal is a member selected from the group consisting of silicon (Si), aluminum (Al), iron (Fe), titanium (Ti), calcium (Ca), magnesium (Mg), sodium (Na), potassium (K), sulfur (S), and phosphorous (P).

* * * * *